US010292772B2

(12) United States Patent
Wei et al.

(10) Patent No.: US 10,292,772 B2
(45) Date of Patent: May 21, 2019

(54) METHOD AND SYSTEM FOR DETERMINING OPTIMAL TIMING FOR SURGICAL INSTRUMENT INSERTION IN IMAGE-GUIDED SURGICAL PROCEDURES

(71) Applicant: EDDA TECHNOLOGY, INC., Princeton, NJ (US)

(72) Inventors: Guo-Qing Wei, Plainsboro, NJ (US); Xin Dou, Princeton, NJ (US); Li Fan, Belle Mead, NJ (US); Cheng-Chung Liang, West Windsor, NJ (US); Jian-Zhong Qian, Princeton Junction, NJ (US); Xiaolan Zeng, Princeton, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 553 days.

(21) Appl. No.: 14/608,267

(22) Filed: Jan. 29, 2015

(65) Prior Publication Data
US 2015/0216616 A1 Aug. 6, 2015

Related U.S. Application Data

(60) Provisional application No. 61/934,291, filed on Jan. 31, 2014.

(51) Int. Cl.
*A61B 19/00* (2006.01)
*A61B 34/20* (2016.01)
(Continued)

(52) U.S. Cl.
CPC .............. *A61B 34/20* (2016.02); *A61B 34/10* (2016.02); *A61B 90/11* (2016.02); *A61B 2034/2074* (2016.02)

(58) Field of Classification Search
CPC .............. A61B 34/20; A61B 17/3403; A61B 2017/00119; A61B 2017/00699;
(Continued)

(56) References Cited

U.S. PATENT DOCUMENTS 6,119,033 A 9/2000 Spigelman et al.
6,314,310 B1 * 11/2001 Ben-Haim ............. A61B 90/36
600/424
(Continued)

OTHER PUBLICATIONS

International Search Report and Written Opinion dated Aug. 28, 2015 in International Application PCT/US2015/13718.
(Continued)

*Primary Examiner* — John H Le
(74) *Attorney, Agent, or Firm* — Pillsbury Winthrop Shaw Pittman LLP (57) ABSTRACT

The present teaching relates to surgical procedure assistance. In one example, a first set of positions of a plurality of sensors are obtained in an image captured prior to a surgical procedure. The plurality of sensors are coupled with a patient's body. One or more second sets of positions of the plurality of sensors are obtained based on information from a tracking device associated with the plurality of sensors. The one or more second sets of positions change in accordance with movement of the patient's body. One or more similarity measures are calculated between the first set of positions and each of the one or more second sets of positions of the plurality of sensors. A timing at which the surgical procedure initiates is determined based on the one or more similarity measures.

21 Claims, 6 Drawing Sheets

(51) Int. Cl.
*A61B 90/11* (2016.01)
*A61B 34/10* (2016.01)

(58) Field of Classification Search
CPC ........ A61B 2034/105; A61B 2034/107; A61B
2034/2074; A61B 34/10; A61B 90/11;
G06F 19/321; G06F 19/3481
USPC .................. 702/150; 600/424, 426, 534, 587
See application file for complete search history.

(56) References Cited

U.S. PATENT DOCUMENTS

| | | |
|---|---|---|
| 7,072,707 B2 | 7/2006 | Galloway et al. |
| 7,747,312 B2 * | 6/2010 | Barrick ................ A61B 5/1077 |
| | | 600/406 |
| 2004/0019274 A1 | 1/2004 | Galloway |
| 2007/0167801 A1 | 7/2007 | Webler |
| 2009/0099472 A1 | 4/2009 | Remmert et al. |
| 2010/0023915 A1 | 9/2010 | Kuduvalli et al. |

OTHER PUBLICATIONS

International Preliminary Report on Patentability dated Aug. 11, 2016 in International Application PCT/US2015/13718.
Extended European Search Report dated Oct. 9, 2017 in European Application 15743247.7.
Office Action dated Jul. 25, 2018 in Chinese Application 201580018396. 5.

* cited by examiner

METHOD AND SYSTEM FOR DETERMINING OPTIMAL TIMING FOR SURGICAL INSTRUMENT INSERTION IN IMAGE-GUIDED SURGICAL PROCEDURES

CROSS-REFERENCE TO RELATED APPLICATIONS

The present application claims priority to U.S. Provisional Application Ser. No. 61/934,291, filed Jan. 31, 2014, entitled "Optimal Time Determination for Needle Insertion in Image-Guided Interventional Procedures," which is incorporated herein by reference in its entirety.

BACKGROUND

1. Technical Field

The present teaching relates to surgical procedure assistance. More specifically, the present teaching is directed methods, systems, and programing for determining optimal surgical instrument insertion timing in image-guided surgical procedures.

2. Discussion of Technical Background

In image-guided interventional procedures, such as needle biopsy or tumor ablation, interventional radiologists place needles or ablation probes based on images taken of the patient immediately before the procedure. For safety reasons, a needle may not be inserted all at once into the target. Rather a needle may be advanced toward the target step-by-step, and after each needle pass, new images are taken of the patient for verification and/or adjustment of needle position and orientation in order to make the next needle advancement. This process is repeated until the target is reached. This is particular true for lesions located close to critical organs, such as major blood vessels, heart, etc. The imaging modalities used for needle guidance may include, but not limited to, computed tomography (CT), magnetic resonance imaging (MRI), or ultrasound (US).

Interventional radiologists make needle insertion or needle advancement based on images. From the time that the images are taken till the time that the radiologists make needle insertion or needle advancement, there may be many of changes to the patient. First, the patient's breathing status at the time of image acquisition may be different from the time of needle insertion. Patient may have made movements, such as twists. All those may affect the target location change. For example, breathing may cause the lesion to move by more than a centimeter when lesion is close to diaphragm of the lung. It is thus important that at the time of needle insertion or needle advancement, the lesion position be similar to that acquired in images, so that the images provide the closest reality. To find a moment at which the patient condition is mostly close to that at the time of image acquisition is highly desirable.

There have been sensing devices that can detect the breathing status of a patient, e.g., U.S. Patent Application Publication No.: 2009/0099472, Gregor Remmert, Gernot Echner, "Respiratory belt system." Interventional radiologists may then monitor the breathing status of a patient to pick a moment which resembles closely the breathing status at the time of image acquisition for needle insertion or advancement. However, since such sensing devices are not synchronized with imaging acquisition device, it is difficult to obtain the exact breathing signal corresponding to the image acquisition. Another way of breath handling is to ask the patient to hold breath both for image acquisition and for needle advancement. However many patients may not be able to hold their breath to do image acquisition, due to their health conditions. Therefore, there is a need to provide an improved solution to solve the above-mentioned problems.

SUMMARY

The present teaching relates to surgical procedure assistance. More specifically, the present teaching is directed methods, systems, and programing for determining optimal surgical instrument insertion timing in image-guided surgical procedures.

In one example, a method implemented on a computing device having at least one processor, storage, and a communication platform connected to a network for surgical procedure assistance is disclosed. A first set of positions of a plurality of sensors are obtained in an image captured prior to a surgical procedure. The plurality of sensors are coupled with a patient's body. One or more second sets of positions of the plurality of sensors are obtained based on information from a tracking device associated with the plurality of sensors. The one or more second sets of positions change in accordance with movement of the patient's body. One or more similarity measures are calculated between the first set of positions and each of the one or more second sets of positions of the plurality of sensors. A timing at which the surgical procedure initiates is determined based on the one or more similarity measures.

In another example, a method implemented on a computing device having at least one processor, storage, and a communication platform connected to a network is disclosed. A first set of positions of a plurality of sensors are obtained in an image captured prior to an operation on an object. The plurality of sensors are coupled with the object. One or more second sets of positions of the plurality of sensors are obtained based on information from a tracking device associated with the plurality of sensors. The one or more second sets of positions change in accordance with movement of the object. One or more similarity measures are calculated between the first set of positions and each of the one or more second sets of positions of the plurality of sensors. A timing at which the operation initiates is determined based on the one or more similarity measures.

In a different example, a system for surgical procedure assistance is disclosed. The system includes a sensor position extraction unit, a sensor position tracking unit, a measurement unit, and a timing determination unit. The sensor position extraction unit is configured to obtain a first set of positions of a plurality of sensors in an image captured prior to a surgical procedure. The plurality of sensors are coupled with a patient's body. The sensor position tracking unit is associated with the plurality of sensors and configured to obtain one or more second positions of the plurality of sensors. The one or more second sets of positions change in accordance with movement of the patient's body. The measurement unit is configured to calculate one or more similarity measures between the first set of positions and each of the one or more second sets of positions of the plurality of sensors. A timing determination unit is configured to determine a timing at which the surgical procedure initiates based on the one or more similarity measures.

Other concepts relate to software for implementing the present teaching on surgical procedure assistance. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory machine readable medium having information recorded thereon for surgical procedure assistance is disclosed. The recorded information, when read by the machine, causes the machine to perform a series of processes. A first set of positions of a plurality of sensors are obtained in an image captured prior to a surgical procedure. The plurality of sensors are coupled with a patient's body. One or more second sets of positions of the plurality of sensors are obtained based on information from a tracking device associated with the plurality of sensors. The one or more second sets of positions change in accordance with movement of the patient's body. One or more similarity measures are calculated between the first set of positions and each of the one or more second sets of positions of the plurality of sensors. A timing at which the surgical procedure initiates is determined based on the one or more similarity measures.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

The present teaching is directed to methods, systems, and programing for determining the optimal timing for surgical instruments (e.g., needles) insertion or advancement in image-guided surgical procedures based on sensor positions. Sensors may be attached to the patient body. This may provide a new way of quantifying patient breathing status. By analyzing the positional changes of these sensors while the patient is breathing, it is possible to find the best moment that resembles mostly the patient's breathing status of image acquisition to make needle insertion or needle advancement. The system can be realized as a specialized and networked system by utilizing one or more computing devices (e.g., mobile phone, personal computer, etc.) and network communications (wired or wireless). In the following, CT image modality will be used as an example of imaging modality. The scope of the present teaching, however, is not limited to the CT imaging modality and can be applied to any known imaging modality such as MRI imaging modality and ultrasound imaging modality.

Figure 1:
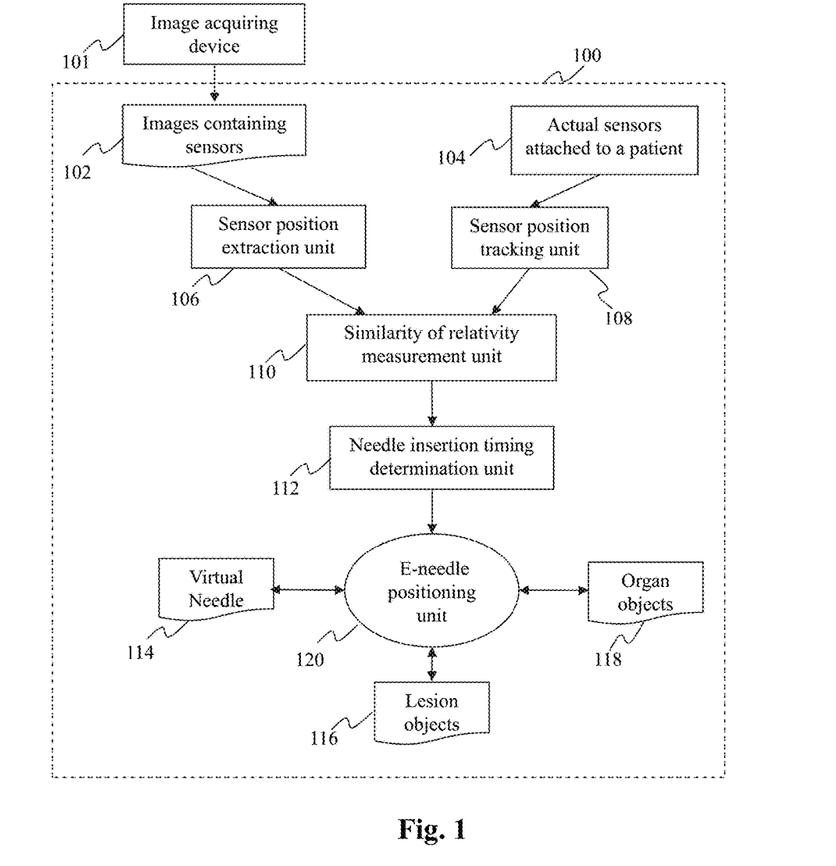
FIG. 1 shows an exemplary system diagram for a surgical instrument insertion timing determination system in image-guided surgical procedures according to one embodiment of the present teaching.

FIG. 1 shows an exemplary system 100 for determining surgical instrument insertion timing, according to an embodiment of the present teaching. The system 100 includes a sensor position extraction unit 106, a sensor position tracking unit 108, a similarity of relativity measurement unit 110, a needle insertion timing determination unit 112, and an electronic needle (e-needle) positioning unit 120. It is understood that although "needle" is described in the present teaching, the surgical instrument insertion timing determination system and method disclosed in the present teaching can be applied to any other suitable instrument used in biopsy and interventional procedures, such as but not limited to probes, knifes, catheters, etc.

Before the patient is scanned by an image acquiring device 101, e.g., a CT scanner in this embodiment, one or more sensors 104 are attached to a patient. In one embodiment, at least three sensors are attached to the patient and used through the procedure. The sensors 104 may be any suitable tracking mechanisms that can detect their poses (positions and/or orientations), such as but not limited to, magnetic sensors or optical sensors. Then the patient is scanned by the CT scanner. The sensor position extraction unit 106 extracts sensor positions from the scanned images 102, e.g., CT images. In some embodiments, the sensors 104 may be capsulated in an enclosure. From the CT images, the entire enclosure may be segmented if it is not easy to segment the exact sensor center directly from the images. Then based on the sensor specifications provided by the sensor manufacturer, the exact sensor location may be determined from the segmented enclosure. The sensor positions in CT images are measured in the CT image coordinates.

In this embodiment, the sensor position tracking unit 108 provides real-time sensor positions of the actual sensors 104 attached to the patient body. The sensor position readings are in the sensor coordinates, which is different from the CT image coordinates. Due to the different coordinates, the absolute sensor positions in the CT images and those obtained by the sensor position tracking unit 108 may not be compared directly. The similarity of relativity measurement unit 110 measures how the sensor positions in the CT images and those obtained by the sensor position tracking unit 108 are similar to each other in terms of "relative positions" (relativity). This measurement may be performed at each time instant of the sensor-position reading from the actual sensors 104 (e.g., at a 50 samples per second rate) during the patient breathing. From the similarity measures, the optimal needle insertion timing may then be found by the needle insertion timing determination unit 112. The similarity measurements may also be displayed as a time-signal in the e-needle positioning unit 120, together with a virtual needle 114, lesion object(s) 116, and organ object(s) 118. In a visual environment generated by the e-needle positioning unit 120, the virtual needle 114 may be moved in response to the movement of the corresponding actual needle (a physical needle) with one or more sensors attached thereon, as described in, e.g., U.S. Patent Application Publication No.: 2012/0029387, Guo-Qing Wei, Jian-Zhong Qian, Cheng-Chung Liang, Xiaolan Zeng, Li Fan, Feng Ma, "Methods and systems for real-time surgical procedure assistance using an electronic organ map," which is incorporated by reference in its entirety.

Figure 2:
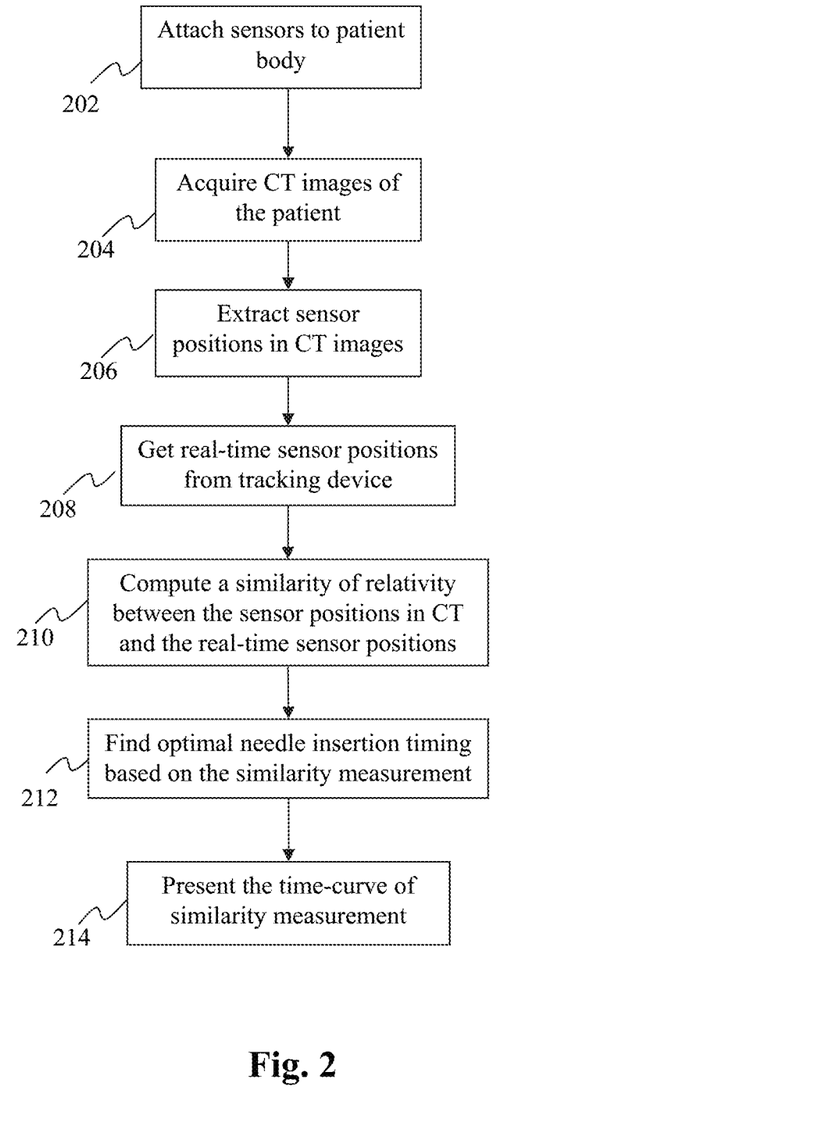
FIG. 2 shows an exemplary flowchart of a process for determination of optimal timing for needle insertion according to one embodiment of the present teaching.

FIG. 2 illustrates an exemplary flow diagram for determining the optimal needle insertion timing, according to one embodiment of the present teaching. At 202, sensors are attached to the patient body, e.g., by clipping the sensors on the patient's skin. In one example, the sensors are distributed widely on the patient body to catch major patient breathing or movement. At 204, a CT scan of the patient may be performed to acquire CT images. From the CT images, sensor positions may be extracted at 206. At 208, real-time sensor positions may be read from the tracking device. These are the same sensors used during the CT image acquisition, and the sensors may be kept on the patient body during the whole procedure. It is noted that the patient may have moved after the CT image acquisition. For example, the table on which the patient lies may slide on a track to move the patient into the gantry of the CT scanning machine. Thus, the absolute sensor positions may change accordingly because of such movement. At 210, a similarity of relativity between the CT sensor positions and the real-time sensor positions may be computed. This similarity measure may be computed at each time instant at which the actual sensors provide positional measurements. At 212, the optimal needle insertion timing may be found by searching for the highest similarity value. Alternatively, a threshold of the similarity measure may be specified so that when the similarity is above the threshold, the needle insertion or advancement may be allowed. At 214, the similarity measure as a function of needle insertion timing may be displayed as a curve for user's examination.

Figure 3:
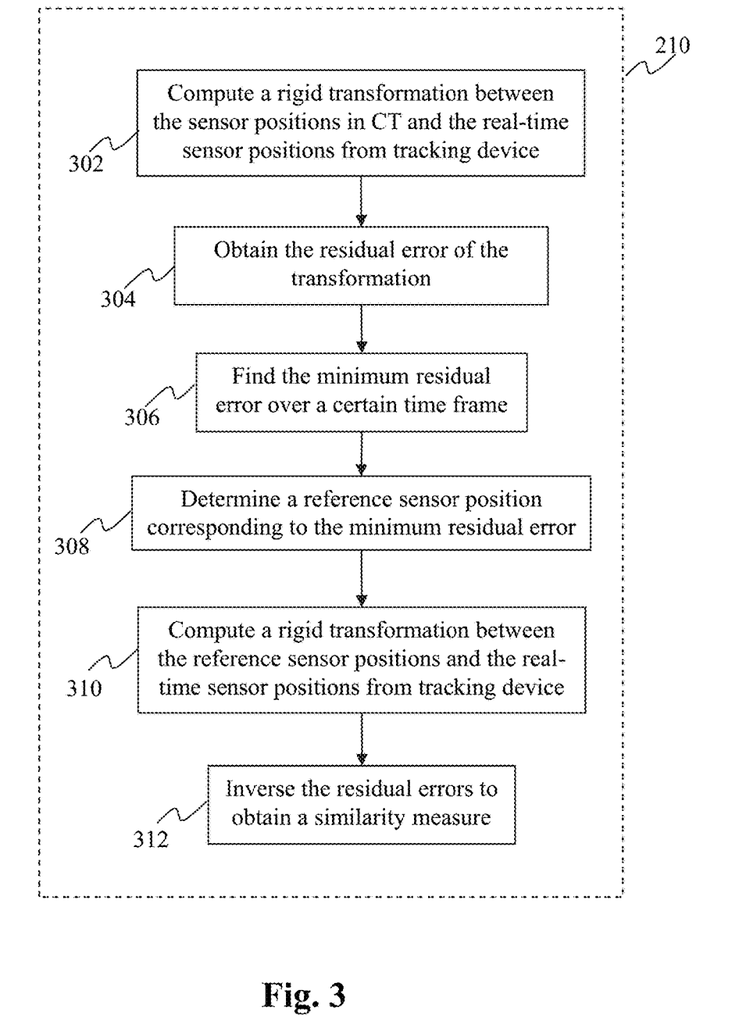
FIG. 3 shows an exemplary flowchart of a process for computation of similarity of relativity between sensor positions based on the residual error of a rigid transformation according to one embodiment of the present teaching.

FIG. 3 shows an exemplary flowchart for computing a similarity measure at 210 according to one embodiment of the present teaching. At 302, a rigid transformation between sensor positions in CT images and the real-time sensor positions read from the tracking device may be computed. This rigid transformation compensates not only the coordinates difference between the CT coordinates and the sensor-device coordinates, but also any shift or rotation movement of the patient. At 304, the residual error of the transformation may be computed. This residual error may be used as an indication of patient's other movement, such as breathing. When the residual error is measured at each time instant, there exists a time point within a breathing cycle at which this residual error is the smallest. Such a time point may correspond to the patient breathing condition closest to that at the time of CT image acquisition. Due to variations of breathing cycle for the same patient and among different patients, a time frame of several breathing cycles may be used to find the minimum residual error at 306. The sensor position corresponding to the minimum residual error is referred as the "reference sensor position" in the present teaching. Due to possible motions other than breathing between the sensor positions in CT images and the reference sensor positions, the obtained minimum residual error may contain contributions from non-breathing motions. To reduce the contributions from non-breathing motions, a rigid transformation between the reference sensor positions and the real-time sensor positions may be computed at 310. The residual error of the transformation may be computed and inversed to provide a similarity measure at 312. It is noted that the computation of reference sensor positions may be repeated after certain time interval, due to possible breathing pattern change over time during the procedure.

Figure 4:
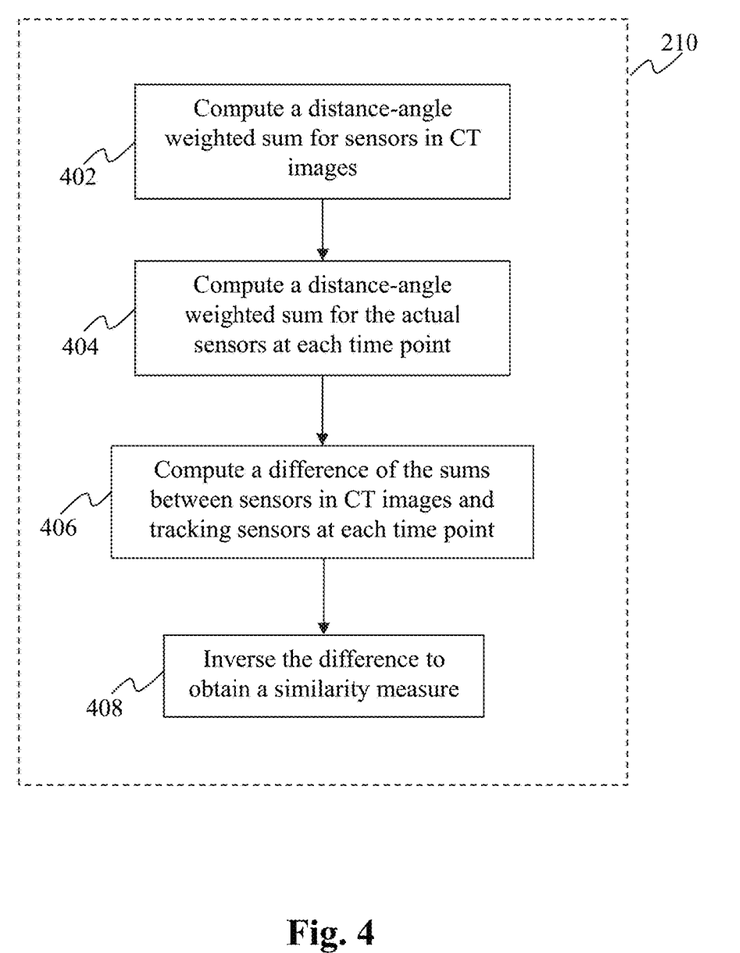
FIG. 4 shows another exemplary flowchart of another process for computation of similarity of relativity between sensor points based on a weighted sum of a distance measure and an angle measure according to another embodiment of the present teaching.

FIG. 4 shows another exemplary flowchart for the similarity measurement at 210, according to another embodiment of the present teaching. At 402, a distance-angle weighted sum may be computed for sensor positions in the CT images. The distance between two points and the angle between two lines are invariant under coordinate transformation. That is, such measures do not change under translation and rotation of the points, and may provide a measure of relativity among points. At 404, the same distance-angle weighted sum may be computed for sensor positions of the actual sensors. At 406, the difference of the sums computed at 402 and 404 may be computed. At 408, the difference may be inverted to provide a similarity measure.

Figure 5:
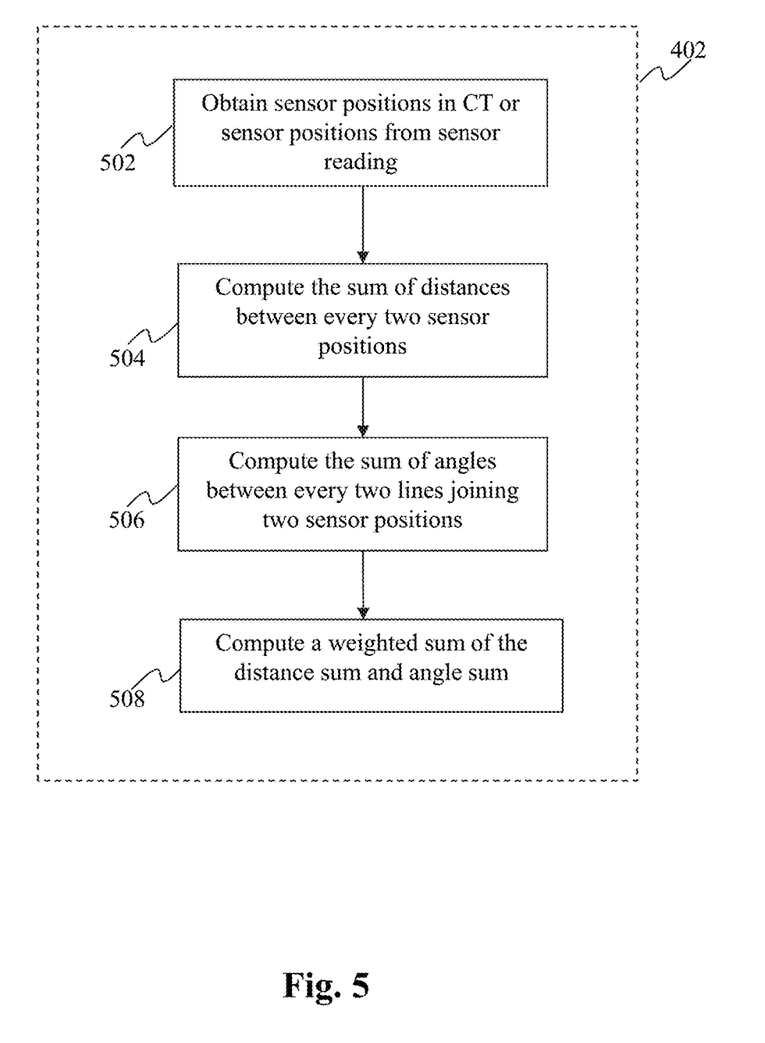
FIG. 5 illustrates an exemplary flowchart of a process for computation of a distance-angle weighted sum between sensor positions according to one embodiment of the present teaching.

FIG. 5 shows an exemplar flowchart for computing a weighted sum of distance-angle measurement. At 502, the sensor positions in CT images and the real-time sensor positions from the actual sensor reading are obtained. In this embodiment, the computation of the weighted sum of distance-angle measurement is the same for both the sensor positions in the CT images and the real-time sensor positions from the actual sensor reading. At 504, the sum of distances between every two sensor positions may be computed. At 506, the sum of angles between every two lines joining two sensor positions may be computed. At 508, a weighted sum of the distance sum and angle sum may be computed. The weight may be determined empirically so that both the distance and angle may contribute equally to the measurement of similarity among points.

To implement various modules, units, and their functionalities described in the present disclosure, computer hardware platforms may be used as the hardware platform(s) for one or more of the elements described herein (e.g., the system 100 described with respect to FIGS. 1-5). The hardware elements, operating systems and programming languages of such computers are conventional in nature, and it is presumed that those skilled in the art are adequately familiar therewith to adapt those technologies to surgical procedure assistance as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 6:
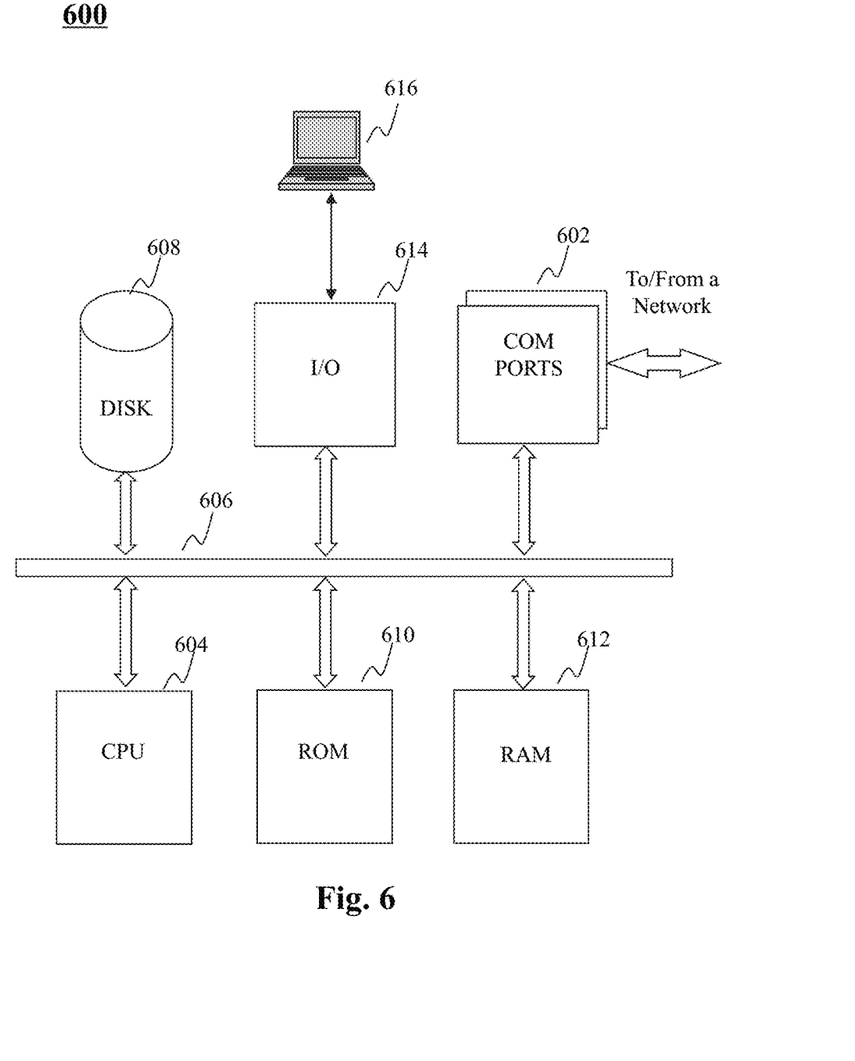
FIG. 6 depicts the architecture of a computer which can be used to implement a specialized system incorporating the present teaching.

FIG. 6 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 600 may be used to implement any component of surgical procedure assistance techniques, as described herein. For example, the system 100 may be implemented on a computer such as computer 600, via its hardware, software program, firmware, or a combination thereof. Although only one such computer is shown, for convenience, the computer functions relating to needle guidance as described herein may be implemented in a distributed fashion on a number of similar platforms, to distribute the processing load.

The computer 600, for example, includes COM ports 602 connected to and from a network connected thereto to facilitate data communications. The computer 600 also includes a central processing unit (CPU) 604, in the form of one or more processors, for executing program instructions. The exemplary computer platform includes an internal communication bus 606, program storage and data storage of different forms, e.g., disk 608, read only memory (ROM) 610, or random access memory (RAM) 612, for various data files to be processed and/or communicated by the computer, as well as possibly program instructions to be executed by the CPU 604. The computer 600 also includes an I/O component 614, supporting input/output flows between the computer and other components therein such as user interface elements 616. The computer 700 may also receive programming and data via network communications.

Hence, aspects of the methods of surgical procedure assistance and/or other processes, as outlined above, may be embodied in programming Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of a search engine operator into the hardware platform(s) of a computing environment or other system implementing a computing environment or similar functionalities in connection with user interest inference. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the surgical procedure assistance system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for surgical procedure assistance, comprising:

obtaining, in a first coordinate system, a first set of positions of a plurality of sensors in an image captured prior to a surgical procedure, the plurality of sensors being coupled with a patient's body;

tracking, by a tracking device, the plurality of sensors to obtain, in a second coordinate system, one or more second sets of positions of the plurality of sensors, wherein each set of the one or more second sets of positions is obtained at a different time instant, each set corresponding to a change in position of the plurality of sensors caused by movement of the patient's body, the second coordinate system being different that the first coordinate system;

calculating one or more similarity measures between the first set of positions and each of the one or more second sets of positions of the plurality of sensors; and determining a timing at which a surgical device is to be inserted into the patient's body based on the one or more similarity measures, wherein the timing is a time instant corresponding to one of the one or more second set of positions having a largest similarity measure with the first set of positions.

2. The method of claim 1, wherein
a plurality of second sets of positions of the plurality of sensors are obtained in a time period; and
a plurality of similarity measures are calculated between the first set of positions and each of the plurality of second sets of positions in the time period.

3. The method of claim 2, wherein the determined timing corresponds to a time at which any one of the plurality of similarity measures is above a threshold.

4. The method of claim 2, wherein the time period corresponds to one or more breathing cycles of the patient.

5. The method of claim 1, wherein calculating one or more similarity measures comprises: for each of the one or more sets of second positions,
performing a first rigid transformation between the first and second sets of positions;
obtaining a first residual error of the first rigid transformation;
determining a third sets of positions of the plurality of sensors based on the first residual error;
performing a second rigid transformation between the second and third sets of positions of the plurality of sensors;
obtaining a second residual error of the second rigid transformation; and
calculating the similarity measure based on the second residual error.

6. The method of claim 5, wherein
a plurality of residual errors of the first rigid transformation are obtained in a time period; and
the third set of positions of the plurality of sensors corresponds to the smallest one of the plurality of residual errors of the first rigid transformation.

7. The method of claim 6, wherein the time period corresponds to a plurality of breathing cycles of the patient.

8. The method of claim 1, wherein calculating one or more similarity measures comprises: for each of the one or more second sets of positions,
calculating a first distance-angle weighted sum based on the first set of positions;
calculating a second distance-angle weighed sum based on the second set of positions; and
calculating the similarity measure based on a difference between the first and second distance-angle weighted sums.

9. The method of claim 8, wherein a distance-angle weighted sum is calculated based on a first sum of distances between each two positions in a set of positions, a second sum of angles between each two positions in the set of positions, a first weight of the first sum, and a second weight of the second sum.

10. The method according to claim 1, wherein the one or more second set of positions of the plurality of sensors are tracked in a time period corresponding to one or more breathing cycles of the patient.

11. A system for surgical procedure assistance, comprising:
a sensor position extraction unit configured to obtain, in a first coordinate system, a first set of positions of a plurality of sensors in an image captured prior to a surgical procedure, the plurality of sensors being coupled with a patient's body;
a sensor position tracking unit configured to track the plurality of sensors to obtain, in a second coordinate system, one or more second sets of positions of the plurality of sensors, wherein each set of the one or more second sets of positions is obtained at a different time instant, each set corresponding to a change in position of the plurality of sensors caused by movement of the patient's body, the second coordinate system being different that the first coordinate system;
a measurement unit configured to calculate one or more similarity measures between the first set of positions and each of the one or more second sets of positions of the plurality of sensors; and
a timing determination unit configured to determine a timing at which a surgical device is to be inserted into the patient's body based on the one or more similarity measures, wherein the timing is a time instant corresponding to one of the one or more second set of positions having a largest similarity measure with the first set of positions.

12. The system of claim 11, wherein
a plurality of second sets of positions of the plurality of sensors are obtained in a time period; and
a plurality of similarity measures are calculated between the first set of positions and each of the plurality of second sets of positions in the time period.

13. The system of claim 12, wherein the determined timing corresponds to a time at which any one of the plurality of similarity measures is above a threshold.

14. The system of claim 12, wherein the time period corresponds to one or more breathing cycles of the patient.

15. The system of claim 11, wherein the measurement unit is further configured to: for each of the one or more second sets of positions,
perform a first rigid transformation between the first and second sets of positions;
obtain a first residual error of the first rigid transformation;
determine a third sets of positions of the plurality of sensors based on the first residual error;
perform a second rigid transformation between the second and third sets of positions of the sensor;
obtain a second residual error of the second rigid transformation; and
calculate the similarity measure based on the second residual error.

16. The system of claim 15, wherein
a plurality of residual errors of the first rigid transformation are obtained in a time period; and
the third sets of positions of the plurality of sensors correspond to the smallest one of the plurality of residual errors of the first rigid transformation.

17. The system of claim 16, wherein the time period corresponds to a plurality of breathing cycles of the patient.

18. The system of claim 11, wherein the measurement unit is further configured to: for each of the one or more second sets of positions,
calculate a first distance-angle weighted sum based on the first set of positions;
calculate a second distance-angle weighed sum based on the second set of positions; and
calculate the similarity measure based on a difference between the first and second distance-angle weighted sums.

19. The system of claim 18, wherein a distance-angle weighted sum is calculated based on a first sum of distances between each two positions in a set of positions, a second sum of angles between each two positions in the set of positions, a first weight of the first sum, and a second weight of the second sum.

20. A non-transitory machine readable medium having information recorded thereon for surgical procedure assistance, wherein the information, when read by a machine, causes the machine to perform the steps of:
    obtaining, in a first coordinate system, a first set of positions of a plurality of sensors in an image captured prior to a surgical procedure, the plurality of sensors being coupled with a patient's body;
    tracking, by a tracking device, the plurality of sensors to obtain, in a second coordinate system, one or more second sets of positions of the plurality of sensors, wherein each set of the one or more second sets of positions is obtained at a different time instant, each set corresponding to a change in position of the plurality of sensors caused by movement of the patient's body, the second coordinate system being different that the first coordinate system;
    calculating one or more similarity measures between the first set of positions and each of the one or more second sets of positions of the plurality of sensors; and
    determining a timing at which a surgical device is to be inserted into the patient's body based on the one or more similarity measures, wherein the timing is the time instant corresponding to one of the one or more second set of positions having a largest similarity measure with the first set of positions.

21. A method, implemented on a computing device having at least one processor, storage, and a communication platform capable of connecting to a network, comprising:
    obtaining a first set of positions of a plurality of sensors in an image captured prior to an operation on an object, the plurality of sensors being coupled with the object;
    tracking, by a tracking device, the plurality of sensors to obtain one or more second sets of positions of the plurality of sensors, wherein each set of the one or more second sets of positions is obtained at a different time instant, each set corresponding to a change in position of the plurality of sensors caused by a movement of the object;
    calculating one or more similarity measures between the first set of positions and each of the one or more second sets of positions of the plurality of sensors; and
    determining a timing at which a surgical device is to be inserted into the object based on the one or more similarity measures, wherein the timing is a time instant corresponding to one of the one or more second set of positions having a largest similarity measure with the first set of positions.

* * * * *